United States Patent [19]

Cymbaluk et al.

[11] Patent Number: 5,104,570

[45] Date of Patent: Apr. 14, 1992

[54] METHOD FOR PREPARING OLEFIN COMPLEXING REAGENTS AND USE THEREOF

[75] Inventors: Ted H. Cymbaluk, Bartlesville, Okla.; Donald C. Tabler, Fort Collins, Colo.; Marvin M. Johnson; Gerhard P. Nowack, both of Bartlesville, Okla.

[73] Assignee: Phillips Petroleum Company, Bartlesville, Okla.

[21] Appl. No.: 457,122

[22] Filed: Dec. 26, 1989

[51] Int. Cl.$^5$ .................................................. C09K 3/00
[52] U.S. Cl. ......................... 252/182.12; 556/114
[58] Field of Search ................... 252/182.12; 556/114

[56] References Cited

U.S. PATENT DOCUMENTS

| | | | |
|---|---|---|---|
| 2,589,960 | 3/1952 | Ray | 260/677 |
| 2,900,347 | 8/1959 | Foreman | 252/182 |
| 2,943,060 | 6/1960 | Smith | 252/182 |
| 3,284,530 | 11/1966 | Nölken et al. | 260/677 |
| 3,514,488 | 5/1970 | Uobele et al. | 260/677 |
| 3,517,080 | 6/1970 | Beckham et al. | 260/677 |
| 3,517,081 | 6/1970 | Beckham et al. | 260/677 |
| 3,518,322 | 6/1970 | Beckham et al. | 260/674 |
| 3,624,172 | 11/1971 | Adams | 585/478 |
| 3,630,676 | 12/1971 | Davis et al. | 23/204 M |
| 3,754,047 | 8/1973 | Long et al. | 260/677 R |
| 4,025,574 | 5/1977 | Tabler et al. | 260/677 A |
| 4,102,802 | 7/1978 | Johnson et al. | 252/184 |
| 4,106,917 | 8/1978 | Fields et al. | 55/31 |
| 4,129,605 | 12/1978 | Tabler et al. | 260/669 A |
| 4,398,052 | 8/1983 | Tabler et al. | 585/845 |
| 4,400,564 | 8/1983 | Johnson et al. | 585/845 |
| 4,749,412 | 6/1988 | Ciuba et al. | 106/14.23 |

OTHER PUBLICATIONS

Comprehensive Inorganic Chemistry, vol. 1, p. 963, (published 1973 by Pergamon Press, Ltd.).
Comprehensive Inorganic Chemistry, vol. 3, pp. 31–32, (published 1973 by Pergamon Press, Ltd.).
J. W. Mellor, A Comprehensive Treatise on Inorganic and Theoretical Chemistry, vol. III, p. 158, (1928).
Kovshov et al., Chem. Abs., 99 (1983) abs. #54817j.
Shehetinina et al., Chem. Abs., 103 (1985) abs. #188477h.

*Primary Examiner*—Edward A. Miller
*Attorney, Agent, or Firm*—Beverly M. Dollar

[57] ABSTRACT

Olefin complexing reagents comprising Cu(I) carboxylate/BF$_3$ adducts in aromatic solvents and a method of preparation therefor, and use of said reagents in the separation of olefins from paraffins are provided.

5 Claims, 3 Drawing Sheets

METHOD FOR PREPARING OLEFIN COMPLEXING REAGENTS AND USE THEREOF

FIELD OF THE INVENTION

This invention relates to a process for the separation and recovery of unsaturated aliphatic hydrocarbons from a mixture of unsaturated aliphatic hydrocarbons and saturated aliphatic hydrocarbons.

In another aspect, this invention relates to a novel composition useful as an unsaturated aliphatic hydrocarbon complexing reagent, and a method of preparation therefor.

BACKGROUND OF THE INVENTION

A separations problem which has required and received considerable attention is that of separating unsaturated aliphatic hydrocarbons such as olefins from close boiling and difficulty separable saturated aliphatic hydrocarbons such as paraffins. Many processes have been proposed for such separations including liquid-liquid extraction, extractive distillation, as well as complex formation. With respect to complex formation, various complexing reagents have been described in the prior art. However, difficulties exist with the previously known systems. For example, aqueous systems involving Cu(I) salts and ammonia or ammonium are corrosive and lack necessary long term stability. Non-aqueous Cu(I) solutions using a pyridine solvent have proven difficult to handle due to the solvent and require large scale systems because the reagent is in the form of a slurry in the solvent. Solvent losses and solvent recovery problems have also been experienced with the non-aqueous systems. Cu(I) sulfonic acid reagents have proven too viscous for easy handling; furthermore the strong heats of absorption of these salts for olefins render the decomplexation difficult. Finally, Cu(I) salt/Lewis acid systems disclosed in the prior art have evidenced solubility problems and solvent alkylation problems.

There exists therefore, the need for a complexing reagent which has a high olefin complexing capacity while providing for easy desorption of the olefin, has a high solubility in an inert solvent, has a favorable viscosity, is relatively stable, gives few side reactions during the complexing process, and can be prepared from cheap starting materials.

It is an object of this invention to provide complexing agents for separation of olefins from paraffins which exhibit good olefin complexing capacity and easy reversibility, and are soluble in an inert solvent.

It is also an object of this invention to provide a method for preparing such complexing reagents from relatively inexpensive starting materials.

It is also an object of this invention to provide a method for separating olefins from a mixture of olefins and paraffins by using the aforementioned complexing reagents.

SUMMARY OF THE INVENTION

In accordance with this invention, it has been discovered that complexing reagents comprising a Cu(I) carboxylate/$BF_3$ adduct in an aromatic solvent are useful for separating olefins from olefin and paraffin mixtures. The complexing reagents of this invention exhibit the desirable properties of high capacity for olefin absorption, low viscosity, easy reversibility and absence of side reactions.

In accordance with one embodiment the complexing reagent is prepared by reacting a copper (II) carboxylate with copper powder in an aromatic solvent under a reducing atmosphere, then adding the $BF_3$ to form the copper (I) carboxylate/$BF_3$ adduct.

In accordance with another embodiment, olefins are separated from a mixture of olefins and paraffins by contacting the mixture with a complexing reagent comprising a Cu(I) carboxylate/$BF_3$ adduct in an aromatic solvent under conditions such that the olefin forms an olefin/reagent complex while the paraffins remain uncomplexed. Then the olefin/reagent complex is separated from the uncomplexed paraffin and, finally, the olefin/reagent complex is treated in order to separate the olefin from the complexing reagent.

DESCRIPTION OF THE PREFERRED EMBODIMENTS

Figure 1:
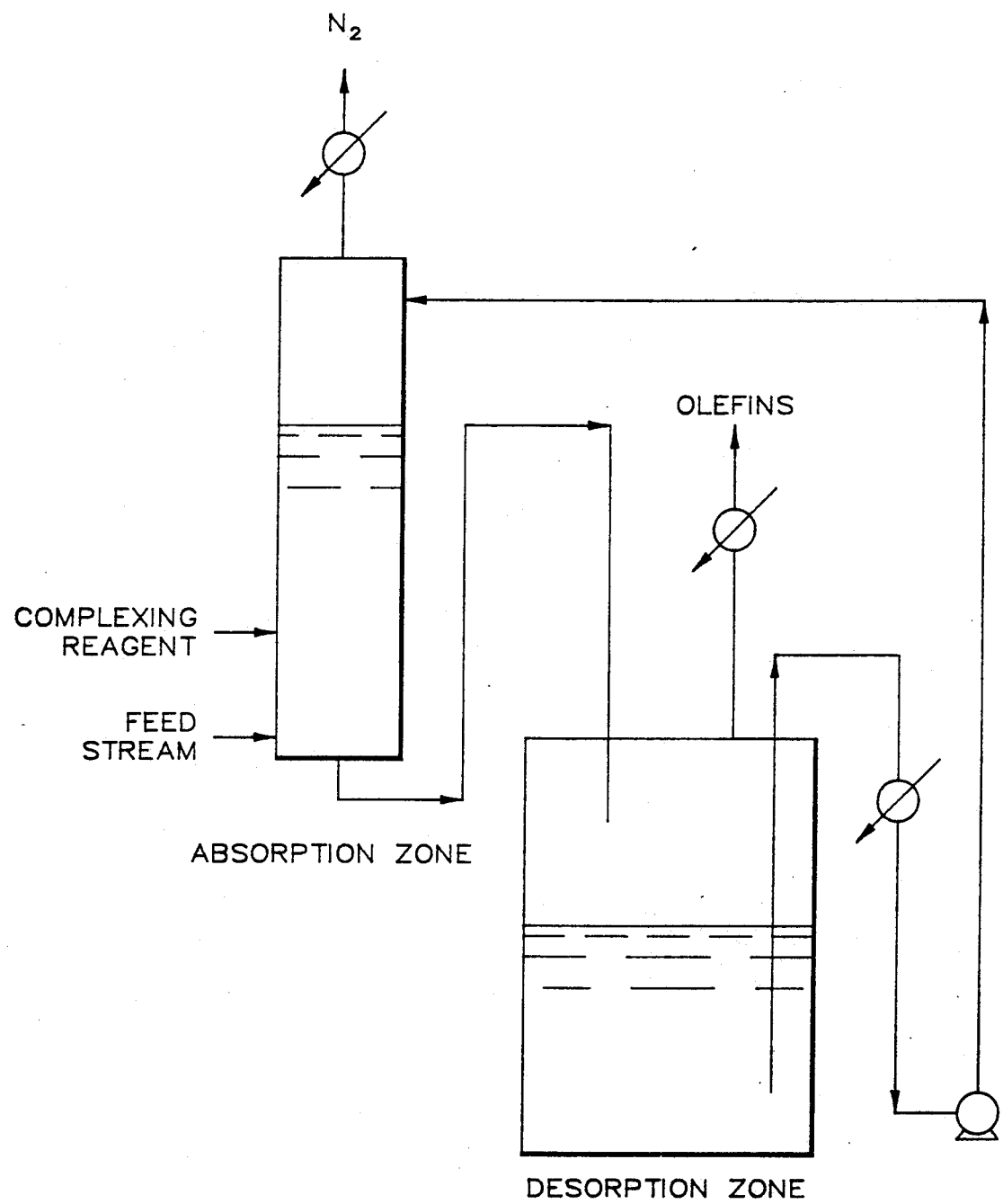
FIG. 1 depicts a schematic of the olefin absorption and desorption process.

The copper (I) carboxylates useful in this invention are the copper (I) salts of mono-, di-, and tri-carboxylic acids containing 1-20 carbon atoms. The carboxylic acid component of the salt can be aliphatic and/or have cyclic or aryl constituents. Suitable examples of copper (I) carboxylates include Cu(I) formate, Cu(I) acetate, Cu(I) propionate, Cu(I) butyrate, Cu(I) pentanoate, Cu(I) hexanoate, Cu(I) octanoate, Cu(I) decanoate, Cu(I) methyl formate, Cu(I) ethyl acetate, Cu(I) n-propyl acetate, Cu(I) n-butyl acetate, Cu(I) ethyl propanoate, Cu(I) octoate, Cu(I) benzoate, Cu(I) p-t-butyl benzoate, and the like. Preferred Cu(I) carboxylates are Cu(I) acetate due to availability and Cu(I) 2-ethyl hexanoate due to the high solubility of the $BF_3$ adduct in hydrocarbon solvents.

The copper (I) carboxylates can be prepared, if necessary, from corresponding anhydrous copper (II) carboxylates by contacting the copper (II) carboxylate with copper powder in an aromatic solvent under a carbon monoxide atmosphere, or by any method known to those of ordinary skill in the art. Otherwise, the copper (I) carboxylate can be used directly in the preparation of the copper (I) carboxylate/$BF_3$ adduct complexing reagent.

The complexing reagent is generally prepared by bubbling or sparging an excess of $BF_3$ through a solution of the copper (I) carboxylate in an aromatic solvent. The preparation is carried out under an oxygen-free inert atmosphere such as nitrogen and in the absence of water.

The molar ratio of $BF_3$ to Cu(I) carboxylate in the adduct is preferably 2:1, however, an excess of $BF_3$ can be present. The Cu(I) carboxylate/$BF_3$ adduct is substantially soluble in the aromatic solvent, thus the amount of $BF_3$ which can be added to the Cu(I) carboxylate solution is that amount necessary to substantially solubilize the Cu(I) carboxylate. Adduct formation is further generally accompanied by a color change in the solution and in some cases, the formation of two immiscible liquid phases.

Excess $BF_3$ can be removed if desired by bubbling or sparging an inert gas such as nitrogen through the solution. The complexing reagent in solution is preferably stored under an inert atmosphere prior to use.

The copper (I) carboxylate is generally employed in the solvent in a concentration in the range of about 0.005 to 3 molar. It is normally desirable to have as much of the copper (I) carboxylate/$BF_3$ adduct in the solution as possible, therefore it is desirable to have as much copper (I) carboxylate in the solution as can be made soluble by contacting with the $BF_3$. At the same time increased concentrations of Cu(I) carboxylate increase solution viscosity; greater solution viscosity can cause pumping and processing difficulties and is to be avoided if possible. Cu(I) carboxylate concentrations in the range of about 0.01 to about 0.5 molar have given highly satisfactory results and are therefore preferred.

The aromatic solvents useful in this invention are hydrocarbons with unsubstituted or alkyl substituted aryl groups, which are normally in the liquid phase under ambient conditions. Suitable examples include toluene, xylene, and the like. The aromatic solvent most preferred is xylene.

The process of the invention is advantageously employed for the separation of mixtures of close boiling light aliphatic hydrocarbons having from 2 to about 25 carbon atoms, preferably from 2 to about 4 carbon atoms. Such separations include the separation of olefin hydrocarbons from paraffin and/or naphthene hydrocarbons and the separation of diolefin hydrocarbons from paraffin and/or naphthene hydrocarbons. The process of the invention is particularly suitable for separating aliphatic monoolefins from close boiling saturated hydrocarbons. The process is preferably utilized for the separation of normally gaseous olefins having from 2–4 carbon atoms from paraffins and the separation of olefins and cycloolefins having from 5–7 carbon atoms from paraffins.

It is also within the scope of this invention to perform a separation of heavier olefins and paraffins which are typically soluble in organic solvents, by choosing an organic solvent in which the olefin/reagent complex is relatively insoluble.

Acyclic and cyclic olefins having from 2 to about 20 carbon atoms per molecule can be separated from paraffins and cycloparaffins by employing the reagent of the invention. Examples include ethylene, propylene, the butenes, 2-pentene, cyclopentene, cyclohexene, cycloheptene, 1-heptene, 1-dodecene, 1-eicosene, 3-methyl-1-butene, 4-methyl-1-pentene, 2,3-dimethyl-2-butene, and the like.

The type of separation contemplated in this invention is the separation of alkenes and cycloalkenes from a paraffin or several paraffins, all components of the mixture having similar boiling points. Examples include the separation of ethylene from ethane, propylene from propane, 1-octene from n-octane, cyclohexene from cyclohexane, and the like.

FIG. 1 depicts a schematic of the olefin absorption and desorption process. The conditions employed in practicing this invention are selected to allow the olefin to react with the complexing reagent to form the complex while minimizing the problem of separating the nonreacted or noncomplexed portion of the feedstream. In the absorption zone, an absolute pressure ranging from about 0.05 to 20 atmospheres, more preferably from about 0.05 to 2 atmospheres, and a temperature ranging from about $-10°$ C. to about $10°$ C. below the boiling point of the solution or slurry of the complexing reagent, preferably from about $30°$ C. to about $25°$ C. below the boiling point of the solution or slurry of the complexing reagent, can be used.

In the desorption zone, the conditions are selected sufficiently different from those used in the absorption zone to promote desorption. Thus, an absolute pressure ranging from about 0.1 to 1.5 atmospheres, more preferably from about 0.5 to 1 atmosphere can be employed. The temperature in this zone can range from about $50°$ C. below the boiling point of the solution or slurry of the reagent to the boiling point of the solution or slurry, more preferably from about $30°$ C. below the boiling point of the solution or slurry of the reagent to the boiling point of the solution or slurry.

The following examples are meant to illustrate the invention and should not be taken to limit the scope thereof.

EXAMPLE I

This example describes the preparation of a Cu(I) propionate/$BF_3$ adduct complexing reagent.

A 1.0 g sample of Cu(I) propionate was placed along with 7.3 cc xylene under a $N_2$ atmosphere in a Diels-Alder tube to form a slurry. $BF_3$ was bubbled through the tube. The solid Cu(I) propionate immediately began to dissolve, forming a dark blue solution. Bubbling was continued until substantially all of the solids dissolved and the solution formed a two phase pale green mixture. The mixture (Cu(I) propionate/$BF_3$ adduct in xylene) was stored under a nitrogen atmosphere before testing in a pressure swing ethylene absorption apparatus. The physical solubility of the olefins in the reagent solvents were separately determined using the pressure swing apparatus in order to correct the absorption data.

The Cu(I) propionate/$BF_3$ complexing reagent was found to effectively complex 2 moles of ethylene per mole Cu.

EXAMPLE II

This example describes the preparation of a Cu(I) octoate/$BF_3$ adduct complexing agent wherein the starting material is a Cu(II) octoate.

A 10 g sample of anhydrous Cu(II) octoate (0.028 moles), 150 cc toluene and 3.6 g (0.0567 moles) Cu powder was added to a 300 cc autoclave. The autoclave was flushed with CO and pressurized to 750 psig. No apparent reaction (indicated by CO uptake) occurred after 30 minutes at room temperature so the temperature was increased to $140°$ C. At this temperature CO uptake was observed in the form of pressure decreases and when no further CO uptake occurred, the autoclave was cooled to room temperature. A sample aspirated out of the vessel revealed a partially soluble light blue solid. The solid was air sensitive, turning blue-green almost immediately upon exposure to air. Addition of water to a portion of the sample brought about immediate Cu° metal formation and a dark blue solution, believed to be due to disproportionation. The Cu(I) octoate formed by the reaction above was further reacted with $BF_3$ to form a Cu(I) octoate/$BF_3$ adduct complexing reagent.

Figure 2:
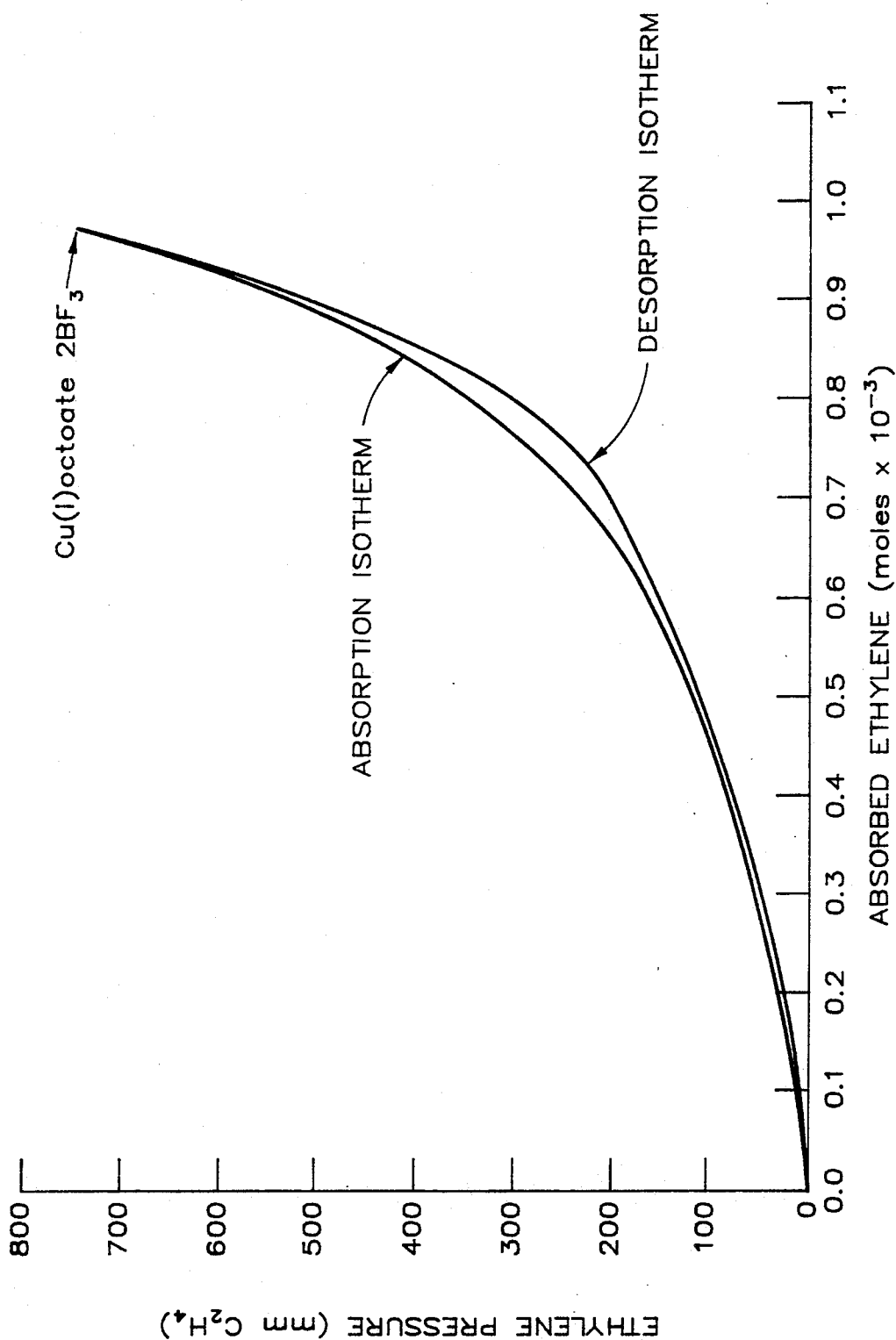
FIG. 2 depicts an absorption isotherm for the complexation of ethylene employing the invention Cu(I) octoate/$BF_3$ complexing reagent.

The reaction mixture from the above procedure was treated with $BF_3$ by pressurizing the autoclave to 30 psig with $BF_3$. After allowing the reaction to proceed at room temperature for several minutes a pressure drop was observed. The temperature was increased to 115° C. to insure complete reaction. No further $BF_3$ uptake was observed and the reaction system was cooled to room temperature, then vented and flushed with nitrogen several times. The product, an amber colored solution, was aspirated into a nitrogen flushed flask and stored under nitrogen. The solution was air sensitive; a sample turned blue-green upon air exposure. Disproportionation to Cu(II) and Cu° metal resulted upon $H_2O$ treatment of a sample. The Cu(I) octoate/$BF_3$ adduct in solution was stored under a nitrogen atmosphere prior to testing in the ethylene absorption apparatus. The Cu(I) octoate/$BF_3$ complexing reagent absorbed 2 moles ethylene per Cu mole. FIG. 2 depicts absorption and desorption isotherms for the complexation of ethylene using the Cu(I) octate/$BF_3$ complexing reagent of this example. This figure demonstrates the easy reversibility obtained using the invention reagent.

EXAMPLE III

This example demonstrates that Cu(I) halide salts do not form complexing reagent adducts with $BF_3$.

A 2.8 g sample of Cu(I)Cl was placed in a nitrogen flushed gas dispersion bottle. About 80 ml of dry toluene was added. The Cu(I)Cl was insoluble in the solvent. $BF_3$ was bubbled through the solution for approximately 5 minutes; and no apparent reaction occurred. After 10 more minutes during which $BF_3$ was bubbled through the solution, the solution appeared to exhibit a brownish or bronze tint, however no appreciable amount of the Cu(I)Cl solid had dissolved.

Additionally, another preparation attempt was made for a Cu(I) halide/$BF_3$ reagent. A 1.43 g sample of Cu(I)Br was added to 10 cc xylene in a Diels-Alder tube. $BF_3$ gas was bubbled through the xylene with the insoluble Cu(I)Br for approximately 1 hour with only a negligible amount of solid dissolving.

Figure 3:
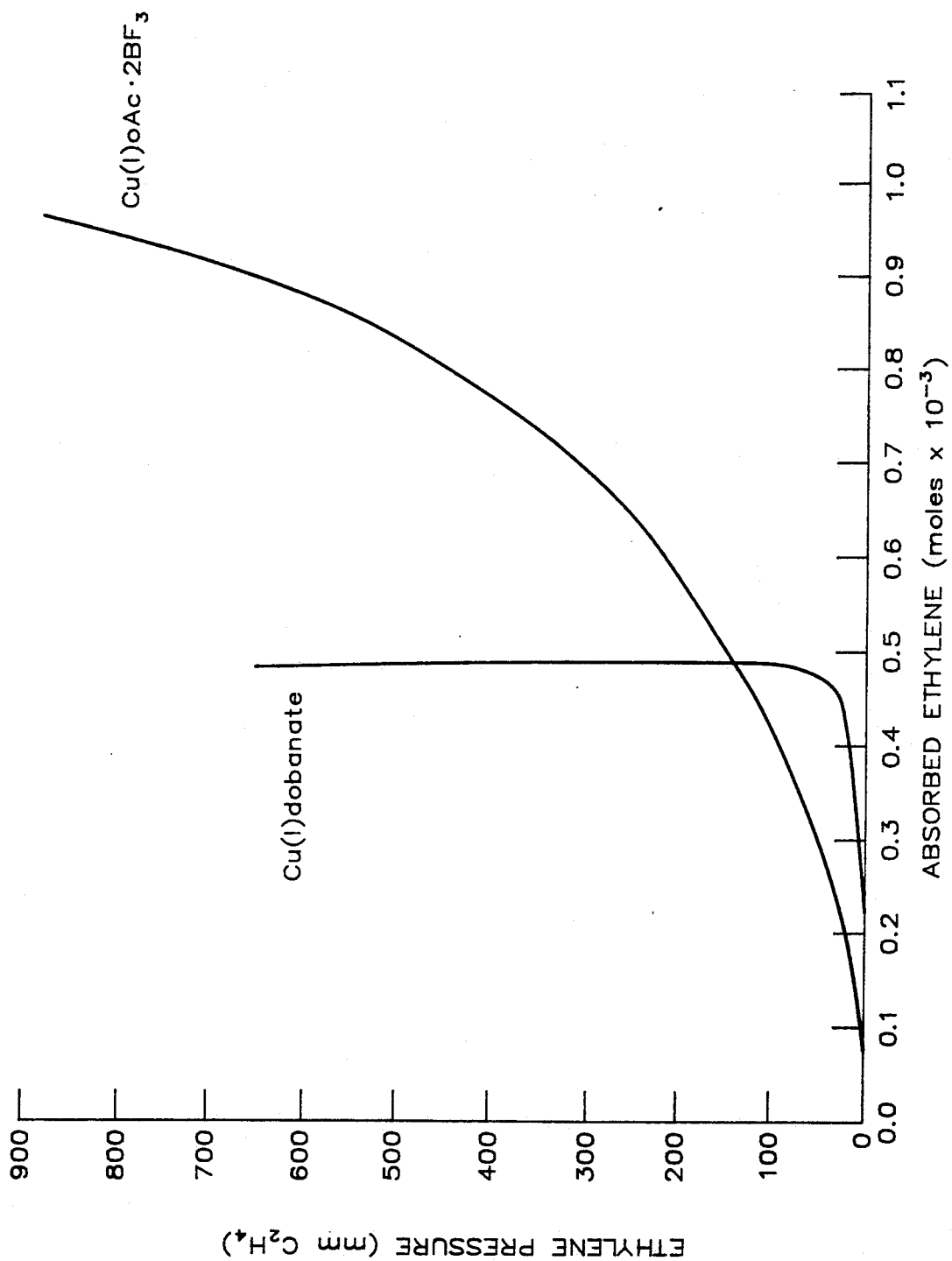
FIG. 3 depicts an absorption isotherm for the complexation of ethylene employing the invention Cu(I) acetate/$BF_3$ complexing reagent.

For comparison purposes, the above procedure was repeated using Cu(I) acetate instead of Cu(I)Cl. A 0.5 g sample of Cu(I) acetate was placed in the nitrogen flushed gas dispersion bottle, then 50 ml dry toluene was added. $BF_3$ was bubbled through the solution, and the previously insoluble Cu(I) acetate immediately began to dissolve. When all the solid had dissolved, the solution was flushed with nitrogen to remove excess $BF_3$, and was then stored under a nitrogen atmosphere prior to testing in the ethylene absorption apparatus. Upon testing, the Cu(I) acetate/$BF_3$ complexing reagent absorbed 2 moles ethylene per mole Cu. FIG. 3 depicts an absorption isotherm for the Cu(I) acetate (Cu(I)OAc/$BF_3$ complexing reagent's absorption of ethylene when compared to that of another complexing reagent, Cu(I) dobanate. FIG. 3 demonstrates that the invention reagent was able to absorb greater amounts of the olefin.

EXAMPLE IV

The replacement of Cu with other metals was investigated.

A 1.67 g sample of silver acetate was added to 10 cc xylene in a Diels-Alder tube. $BF_3$ was bubbled through the xylene solution with the insoluble Ag acetate. After approximately 5 minutes the Ag acetate dissolved, forming a yellowish solution. The tube was flushed with nitrogen to remove excess $BF_3$, then stored under nitrogen prior to testing in the ethylene absorption apparatus. The Ag acetate/$BF_3$ complexing reagent absorbed approximately 1 mole ethylene per mole Ag.

Zn(II) acetate was also tried. A 1.0 g sample of Zn(II) acetate was placed in 10 ml xylene in a Diels-Alder tube. $BF_3$ was bubbled through the xylene solution with the insoluble Zn(II) acetate for approximately 15-20 minutes. No visible change or heat of reaction was observed.

EXAMPLE V

An attempt to form a Cu(II) acetate/$BF_3$ complexing reagent was made.

A 1.82 g sample Cu(II) acetate and 10 ml xylene were placed in a Diels-Alder tube. $BF_3$ was bubbled through the xylene solution with insoluble Cu(II)OAc, however no reaction was observed.

EXAMPLE VI

A complexing reagent containing a Lewis Acid other than $BF_3$ was prepared as follows.

A 1.23 g sample of Cu(I) acetate and a 1.34 g sample of $AlCl_3$ were placed in a Diels-Alder tube. Then 10 cc xylene was added. The solution, initially green, gradually became blue-green while some heat of reaction was observed. After approximately 30 minutes, the solution appeared dark green with a small amount of blue precipitate. Upon testing in the ethylene absorption apparatus, the Cu(I) acetate/$AlCl_3$ complexing reagent absorbed 1 mole ethylene per mole Cu.

EXAMPLE VII

A Cu(I) benzoate/$BF_3$ complexing reagent was prepared as follows.

$BF_3$ was bubbled through a 10 ml xylene slurry of 1.85 g of Cu(I) benzoate in a sealed Diels-Alder tube. After about 10 minutes all of the solid has dissolved resulting in a light greenish solution. Almost immediately a white crystalline precipitate began to form and settle out of solution. Efforts to prepare this compound in a higher volume of toluene also resulted in some precipitate formation although not as much as in the more concentrated system.

Upon testing in the ethylene absorption apparatus, the Cu(I) benzoate/$BF_3$ complexing reagent absorbed approximately 1 mole ethylene per mole Cu.

That which is claimed is:

1. A process for preparing an olefin complexing reagent comprising contacting a copper(I) carboxylate under an inert atmosphere and in an aromatic solvent with an excess of $BF_3$ to form an adduct of the copper(I) carboxylate and $BF_3$, respectively, in a 1:2 molar ratio.

2. A process in accordance with claim 1 wherein said copper(I) carboxylate is copper(I) acetate, said aromatic solvent is xylene, and said adduct is isolated as an emulsion in said xylene solvent.

3. An olefin complexing reagent which consists essentially of a 1:2 molar ratio copper(I) carboxylate/$BF_3$ Adduct in an aromatic solvent.

4. An olefin complexing reagent in accordance with claim 3 wherein said copper(I) carboxylate is copper(I) acetate, and said aromatic solvent is xylene.

5. An olefin complexing reagent in accordance with claim 3 wherein said copper(I) carboxylate is copper(I) octoate and said aromatic solvent is xylene.

* * * * *